United States Patent [19]

Falk et al.

[11] Patent Number: 4,803,081
[45] Date of Patent: Feb. 7, 1989

[54] NEW PHARMACEUTICAL PREPARATIONS WITH EXTENDED RELEASE

[75] Inventors: Karl-Erik L. Falk, Lindome; Sven M. Hugosson, Kungsbacka; Adam Rosinski, Mölndal; John A. Sjogren, Mölnlycke, all of Sweden

[73] Assignee: Aktiebolaget Hassle, Molndal, Sweden

[21] Appl. No.: 34,500

[22] Filed: Apr. 3, 1987

[30] Foreign Application Priority Data

Apr. 11, 1986 [SE] Sweden .................................. 8601624

[51] Int. Cl.$^4$ .............................................. A61K 9/14
[52] U.S. Cl. ..................................... 424/488; 424/480; 424/475; 424/486
[58] Field of Search ............... 424/468, 469, 470, 475, 424/480, 486, 488

[56] References Cited

U.S. PATENT DOCUMENTS 4,562,069 12/1985 Hegasy et al. ..................... 424/497
4,673,564 6/1987 Kawata et al. ..................... 424/494

FOREIGN PATENT DOCUMENTS 2714065 10/1978 Fed. Rep. of Germany.
3024858 1/1981 Fed. Rep. of Germany.
3400106 7/1985 Fed. Rep. of Germany.
WO85/04100 9/1985 PCT Int'l Appl..

OTHER PUBLICATIONS

Chemical Abstracts, vol. 104 (1986) Abstract 174662y.
Chemical Abstracts, vol. 99 (1983) Abstract 128360d.
Chemical Abstracts, vol. 92 (1980) Abstract 135278s.
Chemical Abstracts, vol. 92 (1980) Abstract 82429h.
Chemical Abstracts, vol. 77 (1972) Abstract 39130g.
Chemical Abstracts, vol. 70 (1969) Abstract 17133p.
Chemical Abstracts, vol. 98 (1983) Abstract 221832y.

Primary Examiner—Michael Lusignan
Attorney, Agent, or Firm—Brumbaugh, Graves, Donohue & Raymond

[57] ABSTRACT

An extended release perparation of an active compound with very low solubility containing the active compound dissolved or dispersed in a semi-solid or liquid non-ionic solubilizer and whereby the amount by weight of the solubilizer is at least equal to the amount by weight of the active compound as well as a process for the preparation thereof.

17 Claims, 3 Drawing Sheets

NEW PHARMACEUTICAL PREPARATIONS WITH EXTENDED RELEASE

FIELD OF THE INVENTION

The present invention is related to pharmaceutical extended release preparations of active compounds with very low solubility, especially substituted dihydropyridines, and to methods of preparing such preparations.

The object of this invention is to obtain a solid preparation with high extent of bioavailability and extended release of an active compound which normally has very low solubility.

BACKGROUND OF THE INVENTION

Pharmaceuticals with very poor water solubility present formulation problems due to their slow rate of dissolution. Their efficacy can by severely limited and large interindividual variations of absorption can occur. Examples of drugs with very low solubility are some substituted dihydropyridine compounds such as nifedipine and felodipine. The mentioned dihydropyridines are commonly classified as calcium antagonists, which are widely used for the treatment of cardiovascular disorders such as ischaemic heart disease and arterial hypertension. One of the mentioned dihydropyridines, namely felodipine, has a solubility of only 0.5 mg/l in water. Other examples of drugs with very low solubility are griseofulvin, digoxin, oxazepam, phenytoin and cyclosporine.

Several ways to increase drug absorption have been described in the prior literature. One way is described in DE-A No. 3024858, where a sparingly soluble substituted dihydropyridine, nicardipine, is used in its amorphous form in order to obtain increased absorption of the active compound from the intestine. Another way is described in EP-A No. 47899, where very small crystals of a practically insoluble dihydropyridine, nifedipine, have been used in order to increase the extent of the bioavailability. These methods and others are also described in "Techniques of solubilization of drugs", Ed S. H. Yalkowsky in Drugs and the pharmaceutical sciences, Vol. 12. Of particular relevance to the present invention is that surfactant solubilizing agents may be employed in order to increase the bioavailability of the drugs with very ow solubility. It is stated that the improvement of absorption properties can be ascribed to three processes: (1) increased wetting, (2) increased permeability of membranes and (3) solubilization. The cited publication describes several examples and serves as a good review of the state of the art concerning the solubilizing of drugs, especially in order to increase the bioavailability of drugs with very low solubility.

From DE-A No. 3400106 controlled release preparations are known containing one or more natural, partially synthetic or synthetic polymers, one or more lipophilic and/or hydrophilic solvents or thickeners together with one or more pharmaceutically active compounds. In the examples it is described to use a solubilizer in an amount by weight to the active compound which is much less than 1:1.

In the medical treatment of various diseases, e.g. in the cardiovascular, gastrointestinal and chemotherapeutic field, it is an advantage to have a constant concentration of the administered drug in the blood. Thus an extended release of the drug from the pharmaceutical preparation is wanted.

It is important that the extended release preparation delivers the amount of drug needed to maintain an adequate and even effect during the entire therapeutic dosage interval. This usually means that the drug should be delivered at a constant rate to give an even concentration of administered drug in the blood. This is of specific importance for drugs having a small therapeutic index, that is a small difference between effective and toxic concentration. A delayed and constant release of the drug will also be of importance for locally irritating drugs having potential risk of causing gastrointestinal disturbances when present in large local concentrations or for drugs having a short elimination half-life. In the latter case a less frequent administration and thus better patient compliance (cf. Hayes R. B. et al. Clin.-Pharm.Ther. (1977), 22, p. 125–130) may be obtained with extended release preparations compared with conventional dosage forms.

A drug in extended release form is generally given via the oral route. The preparations should preferably give an extended and reproducible release of drug and contribute to a reproducible absorption, have no toxic or irritating constituents and be suitable also for high dosage drugs. Conventionally, extended release is achieved by controlling dissolution and/or diffusion of medicament from the dosage form. Several materials are employed for this purpose e.g. waxes, fatty materials, polymers, natural, synthetic and semisynthetic gums. Among the gums, hydroxypropyl methylcellulose (HPMC) constitutes an important class because of its pH-independent properties as well as its semisynthetic origin. A review of cellulose ethers in hydrophilic matrices for oral controlled release dosage forms is given by Alderman D. A. Int. J. Pharm. Tech. & Prod. Mfr (1984), 5(3) 1-9. The chemical treatment of HPMC to generate a desired constitution and the use of these qualities are disclosed in U.S. Pat. Nos. 3,087,790, 4,226,849, 4,357,469 and 4,369,172. SE-A-8008646-5 describes a combination of HPMC and hydroxypropyl cellulose which is used to control the release rate of a pharmaceutically active compound.

When a hydrophilic matrix is used the soluble polymer forms a gelatinous layer around the tablet after the exposure of the tablet to gastro-intestinal fluids or saliva. The release of the drug is limited by the rate of water penetration into, and diffusion of drug through, the gel formed (Bamba et al. Int. J. Pharm. (1979), 2, 307). Erosion of the gel structure is also an important release mechanism of a drug from the system. The polymers used have to hydrate rapidly in order to protect the tablet from fast dissolution (Alderman 1984).

The rate of absorption of a drug with very low solubility into the circulation from the intestinal tract is closely related to the rate of dissolution. Since a low dissolution rate generally results in a low extent of bioavailability it is difficult to decrease the rate of absorption, i.e. increase the duration, without at the same time lowering the extent of bioavailability.

DESCRIPTION OF THE INVENTION

Figure 1:
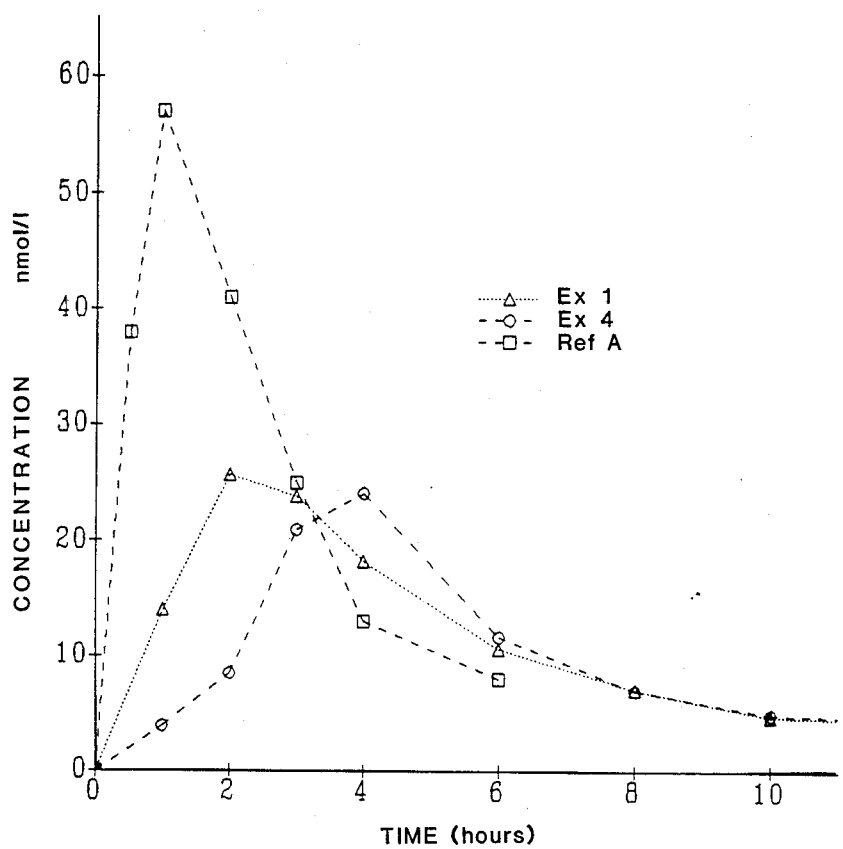
FIGS. 1, 2 and 3 show average plasma values (nmol/l) for various compositions in the Examples.

It is the object of the present invention to provide a preparation of a drug with very low solubility that shows prolonged and nearly constant rate of drug absorption for a long period of time and concurrently maintains a high extent of bioavailability. The obJect is reached by using a solubilizer which is mixed with the drug with very low solubility. The solubilizers suitable according to the invention are defined below. The active compound is preferably dissolved or dispersed in the solubilizer. The mixture of active compound (drug) and solubilizer can be diluted with water or intestinal juice without significant precipitation of the dissolved drug. In the solution the drug is included in a micell-structure formed by the solubilizer. With other commonly used solubilizers or co-solvents dilution may cause precipitation of the drug. The mixture of the drug and the solubilizer is incorporated into a pharmaceutical formulation, which gives prolonged release.

Drugs suitable for the extended release preparation according to the invention are compounds characterized by their very low solubility, that is less than 0.1 per cent by weight in water. In addition they are solubilizable in a solubilizer or in a combination of a solubilizer and water. Examples of drugs suitable according to the invention are some substituted dihydropyridines, such as nifedipine and felodipine. Felodipine is 4-(2,3-dichlorophenyl)-1,4-dihydro-2,6-dimethyl-3,5-pyridinedicarboxylic acid ethyl methyl ester. Nifedipine is 1,4-dihydro-2,6-dimethyl-4-(2-nitrophenyl)-3,5-pyridinedicarboxylic acid dimethylester. Felodipine and nifedipine both are practically insoluble compounds and therefore they are very suitable to solubilize. Other examples of drugs with very low solubility are griseofulvin, digoxin, oxazepam, phenytoin and cyclosporine.

The solubilizers suitable for the preparations according to the invention are semi-solid or liquid non-ionic surface active agents, especially such containing polyethyleneglycols as esters or ethers. The are preferably chosen from polyethoxylated fatty acids, hydroxylated fatty acids and fatty alcohols. It is especially preferred to choose the solubilizer from the group polyethoxylated castor oil, polyethoxylated hydrogenated castor oil, polyethoxylated fatty acid from castor oil or polyethoxylated fatty acid from hydrogenated castor oil. Commercially available solubilizers, which can be used are known under the trade names Cremophor, Myrj, Polyoxyl 40 stearate, Emerest 2675, Lipal 395 and HCO 50. A specially preferred solubilizer is Cremophor ®RH 40 (BASF).

The active compound mixed with the solubilizer is incorporated into different kinds of known controlled release systems, e.g. a hydrophilic gel system, beads coated with a rate controlling membrane, which can be a diffusion retarding coating or a disintegrating coating or tablets with an inert porous matrix. According to the invention the solubilized drug is preferably combined with a hydrophilic gel system, namely a hydrophilic swelling matrix e.g. HPMC. This form of controlled release mechanism is a suitable way to control the release of the micelles of drug and solubilizer. The technical properties are good and also the performance in vivo is good. Among different hydrophilic materials tested, HPMC, hydroxypropyl methylcellulose, is the best gel-forming material. Other examples of suitable compounds effecting the release of the active compound from the hydrophilic gel system are guar gum, xanthan gum, carboxypolymethylene, different cellulosic materials e.g. sodium carboxymethylcellulose and hydroxypropyl cellulose, lactose and aluminium silicate.

The preparation according to the invention contains 20-80% by weight, preferably 30-50% by weight of the hydrophilic gel system.

The major part of the hydrophilic gel system has a viscosity below 100 cps. It is especially preferable to use HPMC having a hydroxypropoxyl content of 4-12% by weight, especially about 8.5% by weight and a viscosity lower than 100 cps, e.g. 6,15 and/or 50 cps. The viscosity is measured by a standardized method described e.g. in United States Pharmacopeia XXI, 1985, p. 672.

The final preparation is e.g.in the form of a gel tablet. By a careful choice of fillers and binders as well as gel forming material the preparation can be manufactured into a commercially acceptable form, e.g. a tablet or a hard gelatin capsule comprising the gel forming granulate, that shows unexpectedly good absorption of the active compound as well as a prolonged duration of action. In the preparation according to the invention the proportions between the active compound and the solubilizer varies in the range from 1:1 to 1:10, preferably in the range from 1:2 to 1:6.

Also other types of controlled release preparations may be used according to the invention e.g. tablets with an inert porous matrix; capsules comprising granules with a diffusion retarding coating or a disintegrating coating.

The tablets with an inert porous matrix are obtained by mixing the drug and the solubilizer with water insoluble polymers or waxes and with fillers and binders. Polyviny.lacetate, polyvinylchloride, ethylcellulose, paraffin and cellulose acetate phthalate could be used as suitable diffusion-retarding polymers. The fillers and binders are solid, powdered carriers such as lactose, saccharose, sorbitol, mannitol, starch, amylopectin, cellulose derivative, gelatine or other suitable carrier. The mixture is moistened with a solvent, e.g. water or ethanol or a solution consisting of e.g. water and a polymer e.g. polyvinylpyrrolidone. Also a lubricating agent e.g magnesium stearate, calcium stearate, sodium stearyl fumarate and polyethyleneglycol wax may be added. The mixture is then formed to tablets.

The capsules comprising of granules with extended release characteristics are obtained by making a core material consisting of the drug and the solubilizer together with fillers. The surface of the core is then coated with diffusion-retarding water insoluble polymers or waxes. The granules are then filled into hard gelatine capsules. The core material could e.g. be prepared by mixing the drug and the solubilizer with carefully selected fillers such as lactose, sorbitol, starch, cellulose derivatives or other suitable fillers. The mixture is moistened with a solvent, e.g. water or ethanol or a solution consisting of e.g. water and a polymer e.g. polyvinylpyrrolidone. The mass is formed to granules e.g. by extrusion and spheronization. The surfaces of the cores formed are coated with a solution consisting of a solvent e.g. methylene chloride and/or isopropyl alcohol and water insoluble polymers e.g. ethylcellulose. The granules are filled in hard gelatine capsules.

EXAMPLES

The following examples illustrate the invention:

EXAMPLE 1

|  | g |
| --- | --- |
| Felodipine | 10 |

| -continued | |
| --- | --- |
| | g |
| Cremophor RH 40 | 90 |
| Calcium phosphate | 250 |
| Hydroxypropyl methylcellulose 2910 6 cps | 250 |
| Xanthan gum | 25 |
| Guar gum | 25 |
| Sodium stearyl fumarate | 13 |

The composition according to Example 1 was formed to hydrophilic matrix tablets containing 10 mg of felodipine/tablet. The tablets were prepared in the following way:

Felodipine was dissolved in Cremophor RH 40 and the solution obtained was carefully mixed with the carrier materials, HPMC, xanthan gum, guar gum and calcium phosphate. The mixture was granulated with ethanol and dried. Sodium stearyl fumarate was added as a lubricant and tablets were prepared by compression in a tabletting machine.

EXAMPLE 2

| | g |
| --- | --- |
| Felodipine | 10 |
| Cremophor RH 60 | 90 |
| Aluminium silicate | 100 |
| Paraffin | 80 |
| Hydroxypropyl cellulose | 7.4 |
| Sodium stearyl fumarate | 5.0 |

The composition according to Example 2 was formed to controlled release tablets, inert porous matrix type, containing 10 mg of felodipine/ tablet. The tablets were prepared in the following way:

Felodipine was dissolved in Cremophor RH 60 and the solution obtained was mixed carefully with the carrier materials aluminium silicate and paraffin. The mixture was granulated with a solution of hydroxypropyl cellulose in ethanol and dried. Sodium stearyl fumarate was added as a lubricant and tablets were prepared by compression in a tabletting machine. A controlled release of felodipine was achieved according to the in vitro results, 50% released after 2 hours and 100% released after 6 hours.

EXAMPLE 3

| | g |
| --- | --- |
| Felodipine | 20 |
| Cremophor RH 40 | 100 |
| Polyvinylpyrrolidone | 66.5 |
| Cellulose, microcrystalline | 62 |
| Maize starch | 29.5 |
| Lactose | 157 |
| Ethylcellulose | 36 |
| Hydroxypropyl methylcellulose 2910 6 cps | 12 |
| Gelatin capsules | |

The composition according to Example 3 was formed to controlled release capsules containing 20 mg of felodipine/capsule. The capsules were prepared in the following way:

Felodipine was dissolved in Cremophor and the solution obtained was mixed carefully with the carrier, polyvinylpyrrolidone, cellulose, maize starch and lactose. The mixture was moistened with water and spheronized. The granules obtained were dried and sieved, the fraction 0.71–1.12 mm was used. The cores were coated with ethylcellulose dissolved in a mixture of methylene chloride and ethanol. The coated granules were filled into hard gelatine capsules.

EXAMPLE 4

| | g |
| --- | --- |
| Felodipine | 20 |
| Myrj 51 | 120 |
| Hydroxypropyl methylcellulose 2910 50 cps | 200 |
| Cellulose, microcrystalline | 20 |
| Lactose | 167 |
| Sodium stearyl fumarate | 10.5 |

The composition according to Example 4 was formed to controlled release tablets containing 20 mg of felodipine/tablet. The tablets were prepared in the same way as described in Example 1.

EXAMPLE 5

| | g |
| --- | --- |
| Nifedipine | 20 |
| Cremophor RH 40 | 50 |
| Hydroxypropyl methylcellulose 2910 50 cps | 70 |
| Hydroxypropyl methylcellulose 2910 6 cps | 160 |
| Cellulose microcrystalline | 6 |
| Lactose | 56 |
| Aluminium silicate | 94 |
| Sodium stearyl fumarate | 10 |

The composition according to Example 5 was formed to hydrophilic matrix tablets containing 20 mg of nifedipine/tablet. The tablets were prepared in the same way as described in Example 1.

The best mode of carrying out the invention is at present considered to be Example 5.

REFERENCE EXAMPLE A

The following example illustrates the reference tablet used in in vivo studies

| | g |
| --- | --- |
| Felodipine | 25 |
| Lactose | 250 |
| Methylcellulose | 0.5 |
| Polyvinylpyrrolidone | 1.5 |
| Magnesium stearate | 3 |

The composition according to reference Example A was formed to fast-dissolving, conventional tablets containing 25 mg of felodipine/tablet. The tablets were prepared in the following way:

Felodipine was micronized and mixed with lactose and methylcellulose. The mixture was granulated with water and dried. Polyvinylpyrrolidone and magnesium stearate were added and the mass was compressed to tablets.

REFERENCE EXAMPLE B

| | g |
| --- | --- |
| Felodipine | 66 |
| Methylcellulose | 13 |
| Mannitol | 870 |
| Polyvinylpyrrolidone | 30 |
| Cellulose, microcrystalline | 40 |
| Ethylcellulose N 10 | 34 |

| | g |
|---|---|
| Polyethyleneglycol 6000 | 41.8 |

The composition according to Reference Example B was formed to controlled release capsules containing 10 mg felodipine/capsule. The capsules were prepared in the following way:

Felodipine was micronized and carefully mixed with the carrier, mannitol, methylcellulose, polyvinylpyrrolidone and cellulose. The mixture was moistened with water and spheronized. The granules obtained were dried and sieved, the fraction 0.71–1.12 mm was used. The cores were coated with ethylcellulose and polyethyleneglycol dissolved in a mixture of methylene chloride and isopropyl alcohol. The coated granules were filled into hard gelatine capsules.

Biopharmaceutical studies

Felodipine

In the attached FIG. 1 the average plasma values (nmol/1) for the compositions according to Example 1, 4 and Reference Example A have been illustrated. A single dose of 20 mg felodipine in a controlled release preparation according to the present invention was administered to 6 healthy male subjects. The plasma concentrations of felodipine were compared with the plasma concentrations after a single dose of a fast dissolving tablet containing 25 mg of felodipine. As can be seen the preparations according to the invention gave lower peaks in the plasma concentration whereas the fast-dissolving tablet gave an unwanted high peak.

The area under the plasma concentration curve (AUC) from time 0 to infinity was

| Preparation | Dose mg | AUC/dose nmol·$h^{-1}$·1·$mg^{-1}$ |
|---|---|---|
| Reference A | 25 | 7.2 |
| Example 1 | 20 | 8.8 |
| Example 4 | 20 | 7.4 |

As can be seen from this table the bioavailability of felodipine was not decreased with the controlled release preparations.

Figure 2:
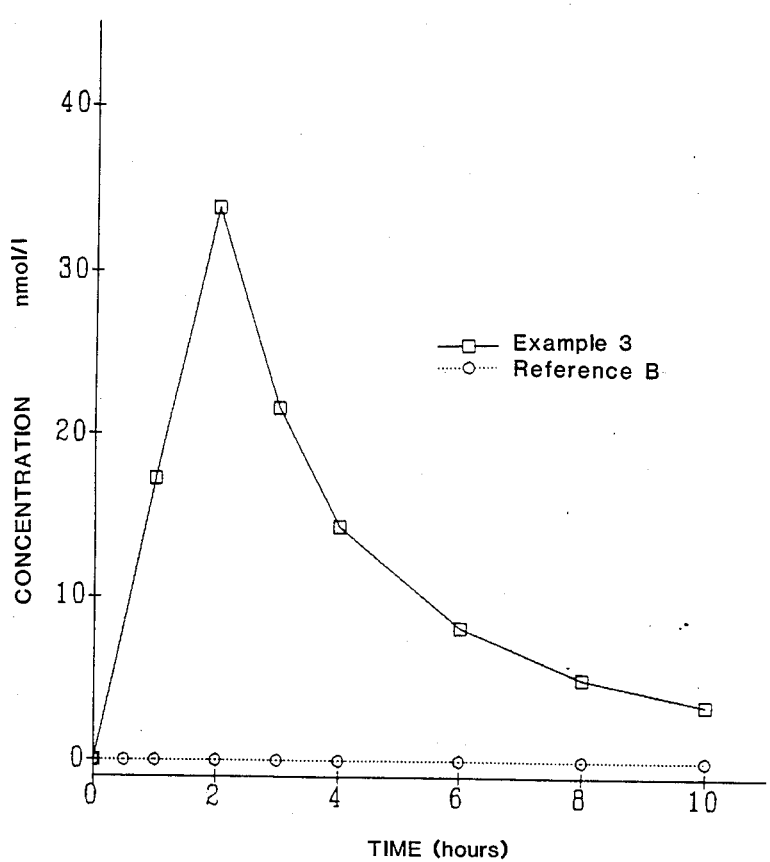

In the attached FIG. 2 the average plasma values (nmol/1) for the compositions according to Example 3 and Reference Example B have been illustrated. A single dose of 20 mg felodipine in a controlled release preparation according to the present invention was administered to 5 healthy male subjects. The plasma concentrations of felodipine were compared with the plasma concentrations after a single dose of a conventional controlled release preparation, that is without the solubilizer, containing 10 mg of felodipine. As can be seen the preparation according to the invention gave a low peak in the plasma concentration and a considerable extent of bioavailability. The Reference gave no detectable plasma concentration which clearly indicates the need of a solubilizer if a controlled release effect is wanted.

Nifedipine

Figure 3:
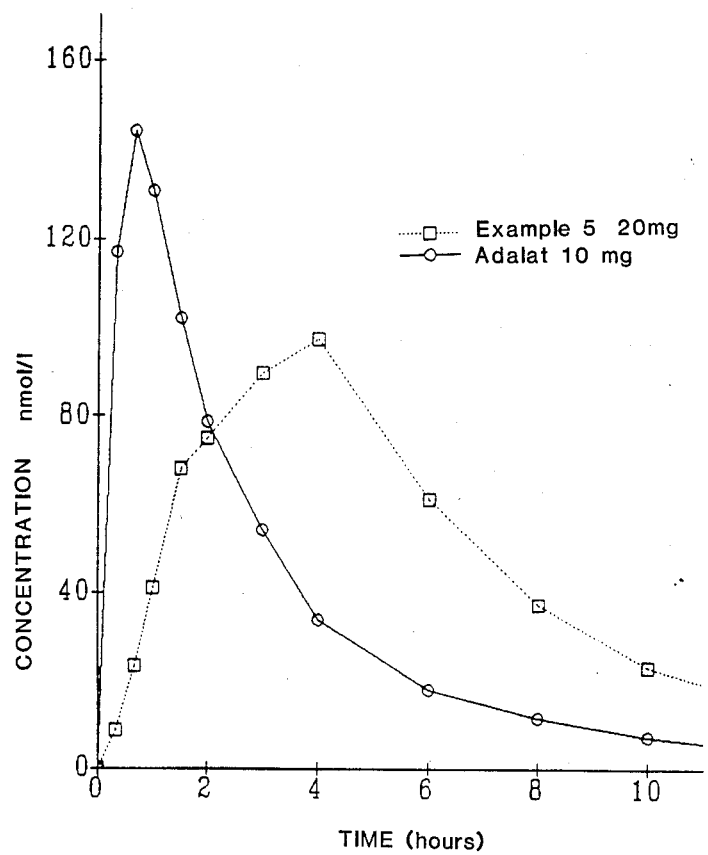

In the attached FIG. 3 the average plasma values (nmol/1) for the composition according to Example 5 and a reference formulation containing nifedipine, Adalat ® 10 mg (Bayer) (Reference C) have been illustrated. Adalat ® is a fast release preparation on the market. A single dose of 20 mg nifedipine in the controlled release preparation according the present invention was administered to 6 healthy male subjects. The plasma concentrations of nifedipine were compared with the plasma concentration after a single dose of the reference formulation containing 10 mg nifedipine. As can be seen the preparation according to the invention gave a lower peak in the plasma concentration, whereas the reference preparation gave an unwanted high peak in spite of the fact that the dose is the half. No substantial reduction in bioavailability can be seen when the Reference C was compared with Example 5.

The area under the plasma concentration curve from time 0 to infinity was:

| Preparation | Dose mg | AUC/dose nmol·$h^{-1}$·1·$mg^{-1}$ |
|---|---|---|
| Adalat ®, Bayer | 10 | 46.5 |
| Example 5 | 20 | 36.0 |

Discussion

The examples above and the attached FIGS. 1, 2 and 3 illustrate the advantages of the controlled release preparation according to the invention in comparison with a conventional preparation or a controlled release preparation without solubilizer, all containing the same active compound. By the solubilization of the active compound with very low solubility it is possible to obtain a tablet having a more constant plasma concentration profile and without any unwanted high peaks. Also an effect during an extended period of time was obtained. Often there is a reduction in the extent of the bioavailability, when drugs with very low solubility are formulated. This invention provides however a technique of making controlled release preparations of drugs with very low solubility with the above-mentioned advantages and without any substantial reduction in the extent of the bioavailability.

We claim:

1. A solid preparation providing extended release of an active compound with very low solubility in water copmrising a solution or dispersion of an effective amount of the active compound in a semi-solid or liquid nonionic solubilizer, wherein the amount by weight of the solubilizer is at least equal to the amount by weight of the active compound, and a release controlling system to provide extended release.

2. A preparation according to claim 1 wherein the non-ionic solubilizer is selected from esters and/or ethers of polyethyleneglycols.

3. A preparation according to claim 1 wherein the non-ionic solubilizer is selected from polyethoxylated fatty acids, hydroxylated fatty acids or fatty alcohols.

4. A preparation according to claim 1 wherein the non-ionic solubilizer is selected from polyethoxylated castor oil, polyethoxylated hydrogenated castor oil, a polyethoxylated fatty acid from castor oil or a polyethoxylated fatty acid from hydrogenated castor oil.

5. A preparation according to claim 4 wherein the non-ionic solubilizer is esters of hydrogenated castor oil fatty acids wit oxyethylated glycerine, especially Cremophor ® 40 (BASF).

6. A preparation according to claim 1 wherein the proportions between the active compound and the solubilizer varies in the range from 1:1 to 1:10, preferably in the range from 1:2 to 1:6.

7. A preparation according to claim 1 wherein the active compound has a solubility in water of 1:1000 or less by weight and is solubilizable in the non-ionic solubilizer or in a combination of water and the non-ionic solubilizer.

8. A preparation according to claim 1 wherein the active compound comprises one or more substituted dihydropyridines.

9. A preparation according to claim 8 wherein the substituted dihydropyridine is nifedipine.

10. A preparation according to claim 8 wherein the substituted dihydropyridine is felodipine.

11. A preparation according to claim 1 wherein the release is controlled by an inert porous matrix, a diffusion retarding coating or a disintegrating coating.

12. A preparation according to claim 1 wherein the release is controlled by a hydrophilic gel system.

13. A preparation according to claim 12 wherein the hydrophilic gelforming component constitutes between 20-80% by weight of the preparation.

14. A preparation according to claim 12 wherein the hydrophilic gel system comprises hydroxypropyl methylcellulose.

15. A preparation according to claim 14 wherein the hydroxypropyl methylcellulose has a hydroxypropyl content of 4-12% by weight.

16. A preparation according to claim 12 wherein the hydrophilic gel system contains carboxypolymethylene.

17. A process for making a solid preparation that provides extended release of an active compound with very low solubility in water comprising dissolving or dispersing an effective amount of the active compound in a semi-solid or liquid nonionic solubilizer, the amount by weight of said solubilizer being at least equal to the amount by wight of the active compound, and incorporating the resulting solution or dispersion into a suitable release controlling system to form a pharmaceutical dosage unit.

* * * * *